United States Patent [19]

Ben-Tovim

[11] Patent Number: 4,856,892

[45] Date of Patent: Aug. 15, 1989

[54] OPHTHALMOSCOPE

[76] Inventor: Nathan Ben-Tovim, 16 Pney Hagiv'a, Ramath Gan, Israel

[21] Appl. No.: 129,310

[22] Filed: Dec. 7, 1987

[51] Int. Cl.[4] .................................................. A61B 3/10
[52] U.S. Cl. ..................................... 351/218; 351/205
[58] Field of Search .................. 351/205, 218; 350/252

[56]  References Cited

U.S. PATENT DOCUMENTS 1,774,382  9/1930  Keeler ................................... 351/218
1,776,960  9/1930  Turville et al. ...................... 351/218
4,603,944  8/1986  Greenlaw et al. ................... 350/252

Primary Examiner—Rodney B. Bovernick
Assistant Examiner—Jay Patrick Ryan
Attorney, Agent, or Firm—Fleit, Jacobson, Cohn, Price, Holman & Stern

[57] ABSTRACT

The invention relates to an ophthalmoscope for indirect ophthalmoscopy. The device contains a light source, a vertically movable condenser and a mirror—preferably—vertically movable.

A lens carrier including a set of lenses can be affixed at will to the ophthalmoscope.

19 Claims, 3 Drawing Sheets

U.S. Patent    Aug. 15, 1989    Sheet 3 of 3    4,856,892
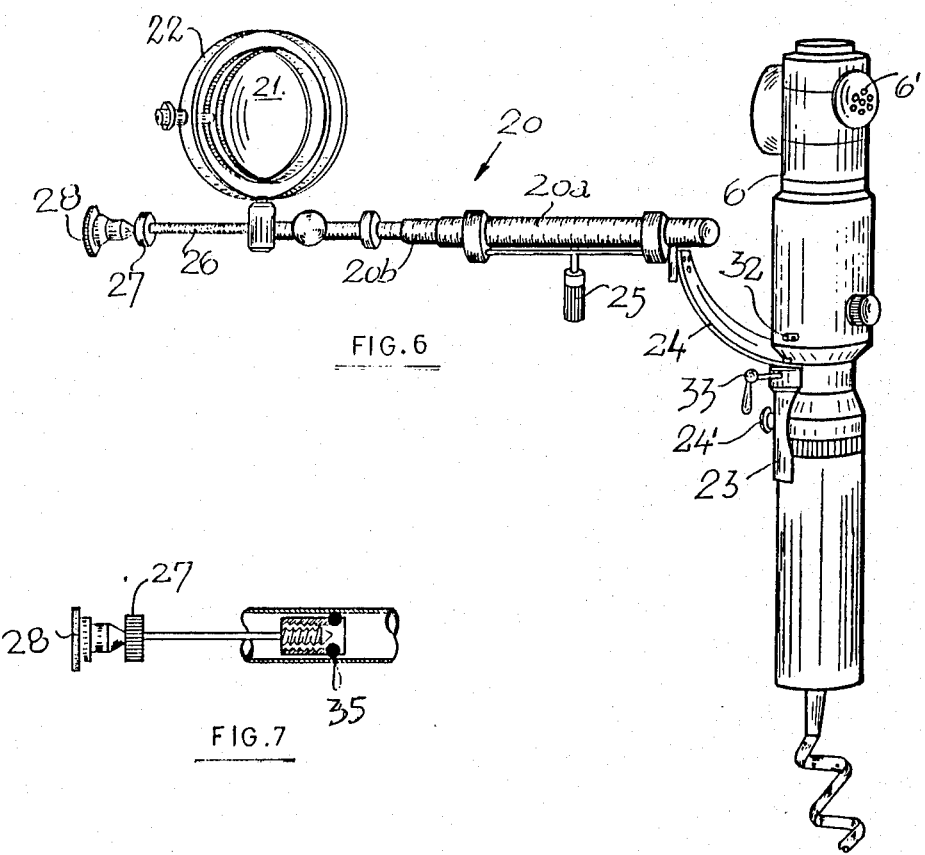
FIG. 6
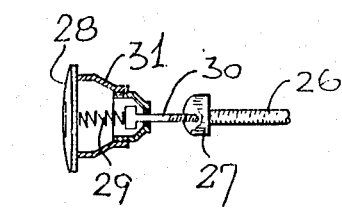
FIG. 7
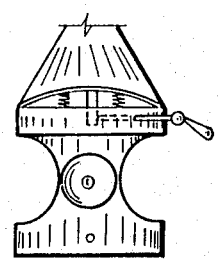
FIG. 9
FIG. 8

OPHTHALMOSCOPE

FIELD OF THE INVENTION

The present invention relates to opthalmoscopes and more particularly to manually held ophthalmoscopes serving the purpose of indirect ophthalmoscopy.

SHORT SUMMARY OF DISCLOSURE

According to the present invention, the hand held opthalmoscope contains at least the following:
1. A light source
2. A mirror, preferably vertically movable.
3. A vertically movable condenser.

By the employ of the last feature an entirely new aspect of ophthalmoscopy (which I shall call 501 Ophthalmoscope and the naure of which will become clear from the following description) can be obtained.

For indirect ophthalmoscopy, the instrument is used with a hand held ophthalmoscopic (condensing) lens or with an attachment carrying such a lens.

It is remarked that a vertically movable mirror in an ophthalmoscope has been described in my U.S. Pat. No. 3,881,812 but the combination thereof with other, new elements which leads to surprising results, has not yet been known.

DETAILED DESCRIPTION OF PREFERRED EMBODIMENT

FIG. 6 is a perspective view of the device in combination with a lens for indirect opthalmoscopy.

FIGS. 7, 8 and 9 show details of the device.

Figure 1:
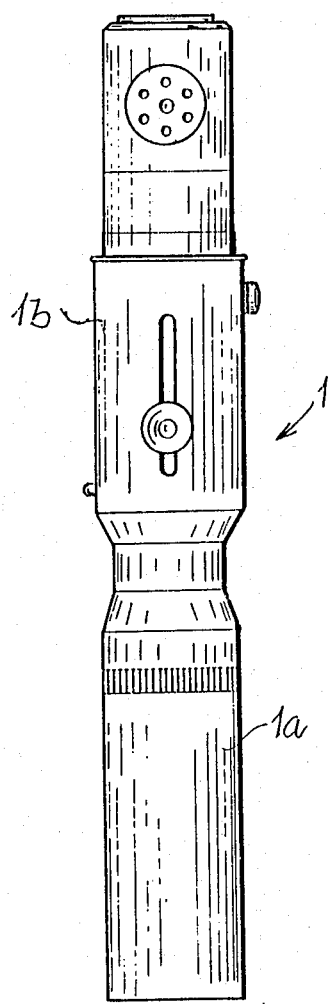
FIGS. 1 and 2 are elevational views of the new device, FIG. 2 being turned through 90° from the position of FIG. 1.
Figure 2:
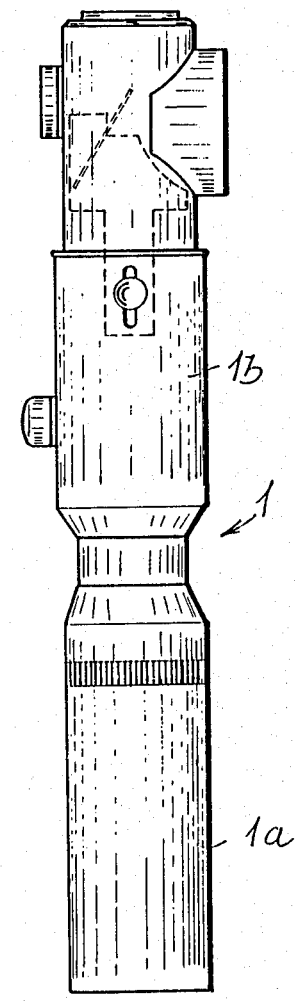
Figure 3:
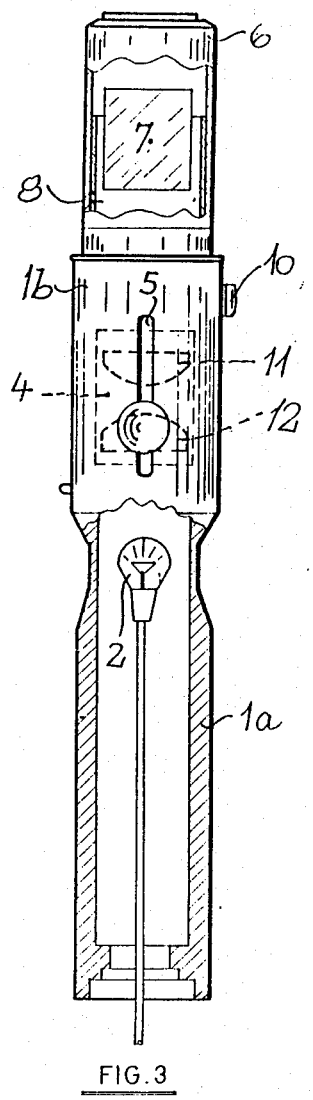
FIG. 3 is a partly sectional view of the device (in the position of FIG. 1).
Figure 4:
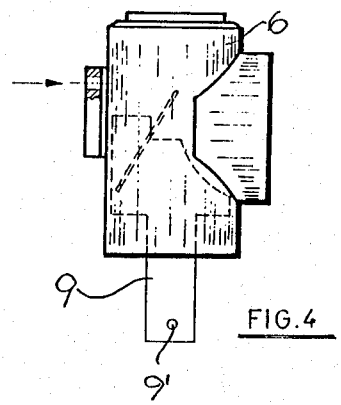
FIG. 4 is an elevational view of the uppermost part of the device.

Turning first to FIGS. 1 and 2, the elongated tubular casing of an ophthalmoscope is indicated as a whole by the numeral 1. It comprises a lower part 1a and an upper 1b. In the conventional way the lower part of casing 1a serves as the handle of the instrument by which the examining physician holds the ophthalmoscope. Within casing 1a is provided a light bulb 2 with straight filament fed with electrical current from the grid via a transformer or a battery, as generally known. A short distance above the bulb 2 is located in part 1b a condenser assembly comprising a sleeve 4 (see also FIG. 5) and two convex lenses 11, 12. Further details of the condenser assembly become clear from FIG. 5 to which reference will be had. A slit 15 is provided in the casing at the level of the condenser assembly.

The casing 1 is topped by a head portion 6 enclosing a mirror 7. A sleeve 8—into which the mirror 7 partly extends—is provided with a simple mechanism by means of which the mirror can be moved vertically i.e. up and down. Sleeve 8 has a downwardly directed extension 9. A shaft (not shown) is affixed to extension 9 at 9'. Shaft 9 bears at its free end a button 10 by means of which the shaft can be slid up and down in a vertical slot in the wall of part 1b.

The vertical movability is useful for facilitating viewing through small pupils (in "up" position) and for eliminating reflexes (in its "down" position) according to Gullstrand.

At the rear of head portion 6 there is a viewing hole and behind the lattr a lens dial 6' containing several convex lenses for alleviating accommodation and for high magnification.

Figure 5:
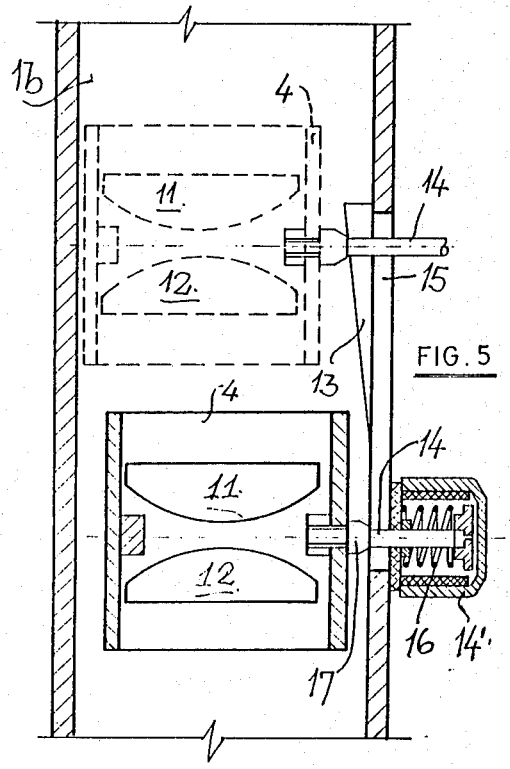
FIG. 5 is a sectional view, on a larger scale, of part of the device.

Reverting now to FIG. 5 showing details of the condenser arrangement, and already referred to, there is seen the casing part 1b and within it the sleeve 4. To sleeve 4 is attached a shaft 14 which extends through slit 15 into the open. On the free end of shaft 14 is set a cap shaped knob 14' in the interior of which is a helical spring 16 urging the knob and the sleeve onto the wall of part 1b.

By means of knob 14' and shaft 14 the condenser can be moved upwards. In its down position, the mirror is largely illuminated by a broad bundle of light, which gives a uniform illumination of the entire fundus. This is especially fit for examination through wide and dilated pupiles. By the upward movement of the condenser, the light of the filament is focussed to a streak of brilliant illumination, variable in width and strength, according to the position of the condenser. The streak can be moved, by small inclinations of the instrument, to chosen areas, all over the fundus, and small details stand out clearly. The streak also penetrates better through opacities, than a diffused light. This "Streak Ophthalmoscopy" is a new dimension in ophthalmoscopic examination.

At the inside wall of part 1b extends in axial direction a ridge 13 facing with an oblique surface the interior of casing 1b, i.e. being directed towards sleeve 4. At the inner end of shafts 14 there is a hemispherical thickening 17. When knob 14 is moved still higher, part 17 begins to slide on ridge 13 causing the sleeve to move forwardly. Thus, both an axial and a forward movement take place. By this, the light spot upon the mirror decreases and moves forwards and finally at the highest position of the knob, the light of the filament is focussed as a minute light streak on the very border of the mirror. By this the instrument is adapted for small pupil viewing. Thus, knob 14' commands three modalities of illumination.

According to FIG. 6 there is attached to the device a lens carrier.

Indirect opthalmoscopy can be performed with the Streak Ophthalmoscope either by means of a hand held ophthalmoscopic (condensing) lens or by means of a special attachment carrying such a lens, the "Lens Carrier", which will now be described.

It is remarked that in U.S. Pat. No. 3,881,812 I have described such a lens carrier, but there are developments to be described now.

This is a horizontal support designated as a whole by numeral 20 and designated to carry interchangeable ophthalmoscopic lenses held in a ring shaped frame 22. It is readily secured to the body of the ophthalmoscope by means of a plate 23 of curved profile and an arcuate arm 24. A set screw 24 affixes plate 23 to the device. Thus all components are integrated into one unit: a hand held indirect ophthalmoscope.

Essentially formed by two telescoping tubes 20a and 20b, the support is variable in length between 18-22 cm by means of a handle 25 fixed to the foremost tube 20b through a list in 20a.

At the distal end of the carrier, there is the said ring shaped frame 22 into which lenses 21 can be instantly fitted. The angular orientation of the lens may be changed at will during the examination.

The most special feature of the lens carrier is the "Distance Fixer" 26 which serves to establish and fix the proper distance between the lens and the observed eye, so as to have the funds picture fill the lens entirely. This is a telescoping rod 26 held inside the foremost tube 20b of the carrier from which it can be drawn out to the desired extent and fixed in position. It bears at its end two parts: a knob 27 and a contact plate 28. Turning knob 27 loosens or fixes the rod 26. This is achieved by two small balls 35 as evident from FIG. 7. The distance fixer is drawn out to its full extent, contact plate 28 is pressed slightly against the cheek of the patient below the examined eye. One approaches gradually until the proper distance is reached and the distance fixer is fixed. Small corrections in the distance can be made during the examination, because the contact plate is spring urged at 29 and yields to slight pressure. This is a "Soft Contact". The physician can operate the indirfct ophthalmoscope single handed, the other hand remaining free for any purpose needed.

According to FIG. 9, the plate 28 is carried on a hollow body 31 in which a spring 29 is positioned. The spring abuts against plate 28 and a headed rod 30. Rod 30 is fixedly connected to knob 27. Body 31 can be screwed towards knob 27 due to screw threads at the end of rod 30 and body 31.

In this case, the Distance Fixer is left loose and the physician plays with its length during the examination, holding knob 27 between his thumb and forefinger, the other fingers resting upon the patient's forehead.

Thus the instrument may perform any desired angular, rotational and small antero/posterior movements while constantly remaining in contact with the cheek and the correct distance is maintained.

To operate the Streak Ophthalmoscope while the carrier is used. the ophthalmoscope must be able to perform certain angular movements in order to bring the streak to any desired spot on the fundus. For this purpose two mechanical arrangements are provided enabling the ophthalmoscope: (1) to tilt forwards and backwards; (2) to rotate to the right and left. By these movements the streak is brought to the extreme limits of the ophthalmoscopic lens and the fundus. Rotation Control Button 32 and Tilt Control Handle 33 control these movements. It is possible to fix the light in any position when a prolongued examination of the spot is needed.

I claim:
1. An ophthalmoscope comprising:
   a casing,
   a source of light located in said casing,
   a vertically movable mirror located in said casing,
   a condenser located in said casing,
   means for simultaneously moving said condenser both in a longitudinal direction of said casing and also crosswise to said longitudinal direction, said means including an oblique surface located on an inside surface of said casing,
   said condenser including a set of lenses accommodated in a sleeve which is carried on a shaft extending across said casing, a portion of said shaft gliding on said oblique surface with the movement of said condenser.
2. The ophthalmoscope claimed in claim 1, wherein said source of light is an incandescent bulb with a straight filament.

3. The ophthalmoscope claimed in claim 1, wherein said casing includes a head portion with a viewing hole having a lens dial located behind said viewing hole, said lens dial containing a number of convex lenses.
4. The ophthalmoscope of claim 1, further comprising a lens carrier fixable to said casing, said lens carrier including a horizontal support to which a ring-shaped frame is fixed into which lenses can be fitted.
5. The ophthalmoscope claimed in claim 4, wherein said horizontal support includes at least two telescoping parts, a handle being fixed to the foremost of said at least two telescoping parts to vary the overall length of said horizontal support.
6. An ophhalmoscope as claimed in claim 5, wherein said telescoping rod has a contact plate at one end.
7. The ophthalmoscope claimed in claim 4, wherein said horizontal support includes a telescoping rod to fix the distance between said lenses and the patient's eye.
8. An ophthalmoscope as claimed in claim 4, wherein said lens carrier includes two mechanisms controlling forwardly and backwardly tilting movements and clockwise and counterclockwise rotational movements.
9. An ophthalmoscope comprising:
   a casing,
   a source of light located in said casing,
   a vertically movable mirror located in said casing,
   a condenser located in said casing,
   means for simultaneously moving said condenser both in a longitudinal direction of said casing and also crosswise to said longitudinal direction,
   a lens carrier fixable to said casing, said lens carrier including a horizontal support to which a ring-shaped frame is fixed into which lenses can be fitted,
   said horizontal support including at least two telescoping parts, a handle being fixed to the foremost of said at least two telescoping parts to vary the overall length of said horizontal support.
10. The ophthalmoscope claimed in claim 9, wherein said means includes an oblique surface located on an inside surface of said casing, said condenser including a set of lenses accommodated in a sleeve which is carried on a shaft extending across said casing, a portion of said shaft gliding on said oblique surface with the movement of said condenser.
11. The ophthalmoscope claimed in claim 9, wherein said source of light is an incandescent bulb with a straight filament.
12. The ophthalmoscope claimed in claim 9, wherein said casing includes a head portion with a viewing hole having a lens dial located behind said viewing hole, said lens dial containing a number of convex lenses.
13. An ophthalmoscope as claimed in claim 9, wherein said horizontal support includes a telescoping rod to fix the distance between said lenses and the patient's eye.
14. An ophthalmoscope comprising:
   an elongated casing,
   a light source located fixed in said casing,
   a mirror located at one end of said casing,
   a condenser located in said casing between said mirror and said light source, and
   means for simultaneously moving said condenser both along a longitudinal axis of said casing and also transverse to said longitudinal axis.
15. An ophthalmoscope as claimed in claim 14, wherein said means includes an oblique surface located on an inside surface of said casing, said condenser including a set of lenses accommodated in a sleeve which is carried on a shaft extending across said casing, a portion of said shaft gliding on said oblique surface with the movement of said condenser.

16. An ophthalmoscope as claimed in claim 14, wherein said mirror is vertically movable.

17. An ophthalmoscope as claimed in claim 14, wherein said casing includes a head portion with a viewing hole having a lens dial located behind said viewing hole, said lens dial containing a number of convex lenses.

18. An ophthalmoscope as claimed in claim 14, further comprising a lens carrier fixable to said casing, said lens carrier including a horizontal support to which a ring-shaped frame is fixed into which lenses can be fitted 19. An ophthalmoscope as claimed in claim 18, wherein said horizontal support includes at least two telescoping parts, a handle being fixed to the foremost of said at least two telescoping parts to vary the overall length of said horizontal support.

* * * * *